United States Patent [19]

Wimmer et al.

[11] Patent Number: 4,985,357
[45] Date of Patent: Jan. 15, 1991

[54] PROCESS FOR THE SYNTHESIS OF GLYCERYL MONONITRATES BY BIOCONVERSION OF NITROGLYCERINE

[75] Inventors: Eric P. Wimmer, Bergerac; Serge L. Lecolier, Janville sur Juine; Claire A. Ducrocq, Orsay; Claudine G. Servy, Palaiseau; Maryse T. Lenfant, Gif sur Yvette, all of France

[73] Assignee: Societe Nationale des Poudres et Explosifs, Paris, France

[21] Appl. No.: 298,035

[22] Filed: Jan. 18, 1989

[30] Foreign Application Priority Data

Jan. 20, 1988 [FR] France ............................... 88 00603

[51] Int. Cl.$^5$ ..................... C12R 1/645; C12R 1/785; C12R 1/90; C12P 13/00
[52] U.S. Cl. .................................. 435/128; 435/123; 435/171; 435/911; 435/931; 435/947
[58] Field of Search ............... 435/128, 171, 911, 931, 435/947, 123

[56] References Cited

U.S. PATENT DOCUMENTS 4,897,351  1/1990  Lenfant et al. ...................... 435/911

Primary Examiner—Herbert J. Lilling
Attorney, Agent, or Firm—Cushman, Darby & Cushman

[57] ABSTRACT

The present invention relates to a process for the preparation of a glyceryl mononitrate or of a mixture of glyceryl mononitrates, characterized in that it comprises a bioconversion step of nitroglycerine to glyceryl mononitrate(s) by a microorganism chosen from the group consisting of the yeasts, the fungi and protozoa, preferably a bioconversion step by fungi.

14 Claims, 1 Drawing Sheet

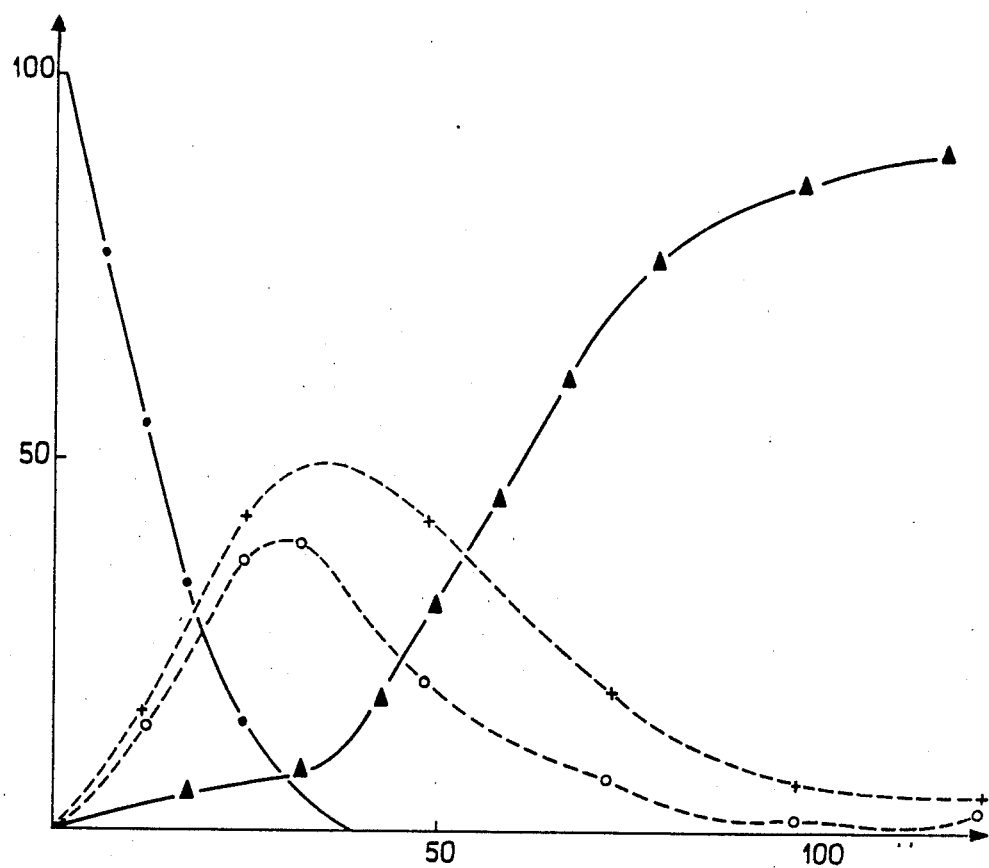

PROCESS FOR THE SYNTHESIS OF GLYCERYL MONONITRATES BY BIOCONVERSION OF NITROGLYCERINE

The present invention relates to a process for the synthesis of glyceryl mononitrates by bioconversion of nitroglycerine.

More precisely, the invention relates to a process for the bioconversion of nitroglycerine (glyceryl 1,2,3-trinitrate or GTN) to a glyceryl mononitrate or a mixture of glyceryl mononitrates.

There are two different glyceryl mononitrates, glyceryl 1-mononitrate (GMN-1) of the formula (1):

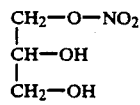

and glyceryl 2-mononitrate (GMN-2) of the formula (2):

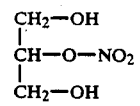

These 2 glyceryl mononitrates have been suggested as medicaments in the treatment of angina pectoris and pulmonary hypertension, in particular in German Patent Nos. 3,514,888 and 3,305,690, especially in the form of sublingual pastilles.

However, the development of these products has been limited by the fact that, to our knowledge, the 2-mononitrate has never been prepared in good yields, but is only obtained in small amounts from the synthesis of the dinitrate.

As far as the 1-mononitrate is concerned, even though a variety of chemical synthesis routes have been suggested, see in particular Rood's Chemistry of Carbon Compounds, second edition p. 17, none of them are satisfactory.

In pharmaco-kinetic studies of the in vivo degradation of nitroglycerine, the formation of traces of mononitrates is mentioned by certain authors, especially P. Needleman and F.E. Hunter (Mol. Pharmacol. 1, 77-86 (1965)).

Furthermore, in Applied and Environmental Microbiology, 36, 5, 693-699 (1978), T. M. Wendt, J. H. Cornell and A. M. Kaplan describe the transitory formation of di and mono-nitrates upon transformation of nitroglycerine to glycerol by bacterial fermentation.

The above investigations clearly indicate that the mononitrates could not be obtained in good yields and all the more so that it was not possible to selectively obtain one of the mononitrates relative to the other since either the product was obtained in traces or the final fermentation product was glycerol.

The applicant has discovered that, in an unexpected manner, certain microorganisms make it possible to obtain the mononitrates starting from nitroglycerine, and even, selectively, one of the mononitrates relative to the other, in increased yields and an increased degree of purity, in a single step in a reaction medium free of any inorganic cations or anions, and without complex purification treatments.

The process according to the invention is a process for the preparation of a glyceryl mononitrate or of a mixture of glyceryl mononitrates, characterized in that it comprises a bioconversion step of nitroglycerine to glyceryl mononitrate(s) by a microorganism chosen from the group consisting of the yeasts, the fungi and the protozoa, preferably a bioconversion step by fungi.

In the process according to the invention, microorganisms producing selectively glyceryl 1-mononitrate (GMN-1) or, alternatively, glyceryl 2-mononitrate (GMN-2) or alternatively microorganisms which allow mixtures of GMN-1 and GMN-2 to be obtained may be used.

Among the many microorganisms which can be used within the scope of the present invention, fungi which must be mentioned in particular are those from amongst the genera Cunninghamella, Geotrichum, Sporotrichum, Phanerochaete, Beauveria and Mucor. The species *Cunninghamella elegans, Geotrichum candidum, Sporotrichum paranense, Geotrichum exile, Phanerochaete chrysosporium, Beauveria tenella, Beauveria bassiana* and *Mucor plombeus* are preferably used.

From amongst the protozoa, representatives of the genus Tetrahymena give good results, for example *Tetrahymena thermophila*.

From amongst the yeasts, interesting representatives are those of the genera Rhodotorula and Hansenula, in particular *Rhodotorula glutinis* and *Hansenula anomala* give good results.

In the application of these microorganisms, it is found that, during the bioconversion step of the nitroglycerine, and contrary to what is reported in the prior art, that the nitroglycerine disappears completely, that glyceryl dinitrates appear and then disappear, and that GMN-1 and/or GMN-2 appear(s) and is (are) then maintained at a constant concentration.

The microorganisms can be applied in free form, in the form of being bound to a support by absorption or in the encapsulated form in a natural or synthetic polymer (alginate or carraghenate, for example following known techniques); in some cases, noncellular extracts may be used.

The bioconversion of nitroglycerine to glyceryl mononitrate(s) is carried out either in an inorganic or organic solution containing the microorganism and nitroglycerine, or, preferably, in a culture medium of the microorganism to which nitroglycerine is added, preferably after the growth phase.

Although many culture media, depending on the microorganism used, can be considered, the medium containing:
a yeast extract,
a malt extract,
and a sugar such as glucose,
is particularly suitable.

Thus, in a liquid medium, a composition containing:

| | |
|---|---|
| a yeast extract | 4-20 g/l |
| a malt extract | 5-15 g/l |
| glucose | 2-50 g/l | may be used.

Good results are obtained by using a culture medium containing Difco Yeast Extract® which is commercially available from Difco Company, as the yeast extract.

According to an advantageous embodiment of the process according to the invention, nitroglycerine is added to the culture medium all at once, in a ratio of 2 to 5 millimoles per liter, preferably 3 to 4 millimoles per liter.

Nitroglycerine may also be added to the culture medium in batches. In this case, the total of GTN applied may be as much as 12 millimoles per liter, which is approximately 2.7 g of nitroglycerine per liter.

The culture conditions have to be adapted to each microorganism.

The most favourable temperature range for the bioconversion is between 20° and 50° C.

However, certain fungi which are called "thermophilic" may be effective at higher temperatures. In this case, the duration of the bioconversion is considerably reduced, which is interesting from the economic point of view.

The pH range which can be used is generally quite wide (3–8) but in some cases it is useful and even indispensible to adjust the pH more specifically depending on the strain used for carrying out the bioconversion.

The conditions of agitation and oxygenation depend on the strain used and are known to those skilled in the art.

As has already been mentioned above, the process allows either a mononitrate mixture or mainly one mononitrate to be obtained.

GMN-1 is obtained using *Cunninghamella elegans* (84% selectivity),

GMN-1 is obtained using *Geotrichum candidum* (65% selectivity),

GMN-2 is obtained using *Sporotrichum paranense* (100% selectivity),

GMN-2 is obtained using *Phanerochaete chrysosporium* (100% selectivity),

GMN-1 is obtained using *Beauveria tenella* or using *Beauveria bassiana* (60% selectivity), GMN-2 and GMN-1 are obtained in equal proportions using *Mucor plombeus* or using *Geotrichum exile*.

Other features and advantages of the process according to the invention will be illustrated by the examples below and by the single figure representing the bioconversion of nitroglycerine by *Geotrichum candidum* CBS 23-376 as a function of time.

EXAMPLE 1

Conversion of trinitroglycerine to glyceryl 2-mononitrate by a culture of *Phanerochaete chrysosporium* ATCC 34541

1—Culture set-up
Composition of the culture medium:

| | |
|---|---|
| Difco Yeast Extract ® | 4 g/l |
| Malt Extract ® | 10 g/l |
| D-glucose | 4 g/l |
| Distilled water | make up to 1 l |
| pH set at 6.8 | |

Difco Yeast Extract ® and Malt Extract ® are yeast and malt extracts marketed by the Difco Company.
Sterilization at 115° C. for 20 minutes.
Preparation of the inoculation solution containing *Phanerochaete chrysosporium* ATCC 34541 at a mean concentration of $5 \times 10^7$ spores/ml, suspended in sterile water, to which a surfactant is added such as the sulphonate which is known under the name of Tween Inoculation of 50 ml of culture medium in a 250 ml conical flask with 1 ml of the inoculation solution.

The culture which is thus obtained is thermostated at 24° C. and shaken on a rotary shaker.

2—Bioconversion 3 days after the inoculation, the following are added under sterile conditions:

Addition of 1 ml of an ethanolic nitroglycerine solution 3% strength (110 micromoles), Addition of 1 ml of the abovementioned nitroglycerine solution 7 days after the first addition.

Addition of 1 ml of the nitroglycerine solution mentioned above 10 days after the second addition.

The nitroglycerine bioconversion is followed with time by high-performance liquid chromatography (HPLC) of aliquot portions of the culture supernatant (C18 column, 10% strength methanol as the eluent).

3—Extraction and isolation of the product

Centrifuging of the culture 12 days after the last addition of trinitroglycerine.

5 successive extractions of the supernatant using ethyl acetate.

Drying of the organic phases over sodium sulphate, followed by evaporation under reduced pressure.

Purification by chromatography on silica.

4—Results

The results which are expressed in µmol, are obtained by comparison with a standard solution containing trinitroglycerine and its hydrolysis derivatives.

The evaluations of the quantities do not take into account the evaporation of the medium, which is not negligible when the culture medium is agitated during the culture phase and the bioconversion phase. The results obtained are collated in Table 1.

GDN-1,3 denotes glyceryl 1,3-dinitrate.
GDN-1,2 denotes glyceryl 1,2-dinitrate.

TABLE 1

Bioconversion of triniroglycerine by *Phanerochaete chrysosporium* ATCC 34541

| Time (days) | GMN-1 µmol | GMN-2 µmol | GDN-1,3 µmol | GDN-1,2 µmol | GTN µmol |
|---|---|---|---|---|---|
| 0 | — | — | — | — | +110 |
| 1 | 4 | 20 | 3 | 83 | <1 |
| 2 | <1 | 50 | 2 | 60 | <1 |
| 3 | <1 | 64 | <1 | 46 | <1 |
| 7 | <1 | 90 | <1 | 18 | <1 +110 |
| 8 | <1 | 70 | 6 | 140 | <1 |
| 9 | <1 | 112 | <1 | 106 | <1 |
| 10 | <1 | 146 | <1 | 73 | <1 |
| 17 | <1 | 165 | 12 | 9 | <1 +110 |
| 18 | <1 | 162 | 8 | 160 | <1 |
| 22 | <1 | 335 | <1 | 24 | <1 |
| 23 | <1 | 311 | <1 | 17 | <1 |
| 29 | <1 | 321 | <1 | 10 | <1 |

Yield of formed product 97%
Yield of isolated product: 40%
GMN-2 selectivity: 100%

The main compound which is obtained in pure form by HPLC corresponds to $C_3H_7NO_5$ according to elemental analysis:

| | % calculated | % measured |
|---|---|---|
| C | 26.3 | 26.22 |
| H | 5.1 | 5.37 |
| N | 10.2 | 10.30 |

The proton NMR spectrum obtained in solution in CDCl₃ shows that this compound corresponds to glyceryl 2-mononitrate (the addition of D₂O causes the 2 peaks which are attributed to the hydrogens of the hydroxyls 1 and 3 to disappear).

EXAMPLE 2

Conversion of trinitroglycerine to a mixture of glyceryl 1-mononitrate and glyceryl 2-mononitrate by *Geotrichum candidum* CBS 23-376

1—Culture set-up

Composition of culture medium identical with that of Example 1.

Sterilization of the medium at 115° C. for 20 minutes.

Inoculation of 250 ml of culture medium in a 2-liter conical flask with $2.5 \times 10^8$ spores of *Geotrichum candidum* CBS 23-376 sampled from pre-cultures in agar tubes.

Shaking of this culture at 24° C. for 3 days on a rotary shaker.

2—Bioconversion

Addition of 3.75 ml of a 4% strength trinitroglycerine solution in ethanol (660 µmol).

Addition identical with the first one, 7 days later.

The bioconversion of the nitroglycerine is followed with time in the same manner as in Example 1.

Example 1.

3-Extraction and isolation of the products

Centrifuging of the culture 6 days after the second addition of trinitroglycerine.

Extraction of glycerol 1-mononitrate and glyceryl 2-mononitrate from the supernatant using $5 \times 100$ ml of ethyl acetate.

By drying and evaporating the organic phases, a residue is obtained.

Transfer of the residue as it is to silica gel.

Separation of the glyceryl mononitrates by elution using a CH₂Cl₂/CH₃OH mixture (95/5).

4—Results

The results are expressed in µmol under the conditions described in Example 1 and are collated in Table 2.

TABLE 2

Bioconversion of trinitroglycerine by *Geotrichum candidum* CBS 23-376

| Time (days) | GMN µmol | GDN-1,3 µmol | GDN-1,2 µmol | GTN µmol |
|---|---|---|---|---|
| 0 | — | — | — | +660 |
| 1 | 10 | 215 | 280 | 150 |
| 2 | 200 | 265 | 190 | <1 |
| 3 | 495 | 110 | 50 | <1 |
| 4 | 540 | 90 | 25 | <1 |
| 7 | 620 | 25 | <1 | <1 +660 |
| 8 | 400 | 530 | 380 | <1 |
| 9 | 570 | 435 | 300 | <1 |
| 10 | 990 | 237 | 92 | <1 |
| 13 | 1,250 | 43 | 21 | <1 |

Yield of mononitrates formed (mixture GMN-1 and GMN-2): 95%
Yield of mononitrates isolated (mixture GMN-1 and GMN-2): 90%
GMN-1 selectivity: 65%

BRIEF DESCRIPTION OF THE DRAWING

The bioconversion of nitroglycerine by *Geotrichum candidum* CBS 23-276 as a function of time is illustrated by FIG. 1 in which: ——.——.—— represents the nicroglycerine concentration.

----x---x--- represents the glyceryl 1,3-dinitrate concentration.

----o----o-- represents the glyceryl 1,2-dinitrate concentration.

——▲—— represents the concentration of GMN-1 plus GMN-2 mixture.

EXAMPLE 3

Conversion of nitroglycerine to glyceryl 1-mononitrate and glyceryl 2-mononitrate by a culture of *Cunninghamella elegans* ATCC 9245

1—Culture set-up

Composition of culture medium identical with that of Example 1.

Sterilization of the culture medium according to the procedures described in Example 1.

Inoculation of 250 ml of culture medium in a 2 liter conical flask with 1 ml of a spore suspension of *Cunninghamella elegans* ATCC 9245 derived from a preculture on a tube of nutrient agar containing a surfactant (Tween 80 ® a concentration of 0.1%).

The culture thus obtained is thermostated at 24° C. and shaken on a rotary shaker.

2—Bioconversion 3 days after inoculation, addition of 5 ml of a 4% strength ethanolic solution of nitroglycerine (724 µmol).

The bioconversion of the nitroglycerine with time is followed using HPLC.

3—Extraction

Following the same procedure as in the examples above.

4—Results

The results are expressed in µmol under the conditions described in Example 1, and are collated in Table 3.

TABLE 3

Bioconversion of trinitroglycerine by *Cunninghamella elegans* ATCC 9245

| Time (days) | GMN-1 µmol | GMN-2 µmol | GDN-1,3 µmol | GDN-1,2 µmol | GTN µmol |
|---|---|---|---|---|---|
| 0 | — | — | — | — | 724 |
| 1 | 55 | 25 | 700 | 275 | <1 |
| 3 | 140 | 30 | 490 | 190 | <1 |
| 10 | 300 | 80 | 260 | 75 | <1 |
| 14 | 355 | 65 | 205 | 65 | <1 |

Yield of mononitrates formed (mixture GMN-1 and GMN-2): 58%
Yield of GMN-1 formed: 49%
GMN-1 selectivity: 84%

EXAMPLE 4

Conversion of nitroglycerine to glyceryl 1-mononitrate and glyceryl 2-mononitrate by a culture of Beauveria bassiana ATCC 7159

1—Culture set-up

Composition of culture medium identical to that of Example 1.

Sterilization of the culture medium according to the procedures described in Example 1.

Inoculation of 50 ml of medium in a 250 ml conical flask with Beauveria bassiana ATCC 7159 spores obtained from a tube of slanted nutrient agar, taken up under sterile conditions in 1 to 5 ml of water containing a surfactant (Tween 80 ® at a concentration of 0.1%).

Culture at 24° C., with continuous shaking.

2—Bioconversion 3 days after inoculation, addition of 1 ml of 3% strength ethanolic solution of nitroglycerine (110 μmol).

The bioconversion of the nitroglycerine as a function of time is followed using HPLC analysis of aliquot portions of the culture supernatant.

3—Extraction

Following the same procedure as in the examples above.

4—Results

The results are expressed in μmol under the conditions described in Example 1 and are collated in Table 4.

TABLE 4

Bioconversion of nitroglycerine by *Beauveria bassiana* ATCC 7159

| Time (days) | GMN μmol | GDM-1,3 μmol | GDN-1,2 μmol | GTN μmol |
|---|---|---|---|---|
| 0 | — | — | — | 110 |
| 1 | 9 | 74 | 81 | 18 |
| 2 | 40 | 123 | 100 | <1 |
| 5 | 75 | 100 | 60 | <1 |
| 6 | 90 | 95 | 55 | <1 |

Yield of mononitrates formed (mixture GMN-1 and GMN-2): 82%
GMN-1 selectivity: 60%

EXAMPLE 5

Conversion of nitroglycerine in glyceryl 2-mononitrate by a culture of *Sporotrichum paranense* 1995 (Museum d'histoire naturelle-Paris) [Paris Museum of Natural History]

1—Culture set-up

Composition of culture medium identical with that of Example 1.

Sterilization of the culture medium according to the procedures described in Example 1.

Inoculation of 50 ml of medium in a 250 ml conical flask with $2 \times 10^7$ spores of *Sporotrichum paranense* 1995 (Museum d'histoire naturelle - Paris).

This culture is agitated continuously at 24° C.

2—Bioconversion

Addition of 1 ml of a 4% ethanolic solution of nitroglycerine (145 μmol) 3 days after inoculation.

3-Extraction and isolation of the products

Centrifuging of the supernatant 21 days after the addition of nitroglycerine.

Saturation with sodium chloride.

Extraction using ethyl acetate.

Drying and evaporation of the organic phase.

Purification of the residue obtained on a silica gel plate.

4—Results

The results are expressed in μmol under the conditions described in Example 1 and are collated in Table 5.

TABLE 5

Bioconversion of nitroglycerine by *Sporotrichum paranense* 1995 (Museum d'histoire naturelle - Paris)

| Time (days) | GMN-1 μmol | GMN-2 μmol | GDN-1,3 μmol | GDN-1,2 μmol | GTN μmol |
|---|---|---|---|---|---|
| 0 | — | — | — | — | 145 |
| 1 | 0 | 5 | 10 | 40 | 20 |
| 8 | <1 | 70 | 20 | 120 | <1 |
| 15 | <1 | 90 | 6 | 45 | <1 |
| 21 | <1 | 105 | 7 | 30 | <1 |

Yield of GMN-2 formed: 73%
GMN-2 selectivity: 100%
Yield of GMN-2 isolated: 40%

EXAMPLE 6

Conversion of nitroglycerine to glyceryl 1-mononitrate and glyceryl 2-mononitrate by a culture of *Mucor plombeus* CBS 24658

Under the same conditions as described in Example 1, a culture is established by inoculating 50 ml of culture medium with *Mucor plombeus* CBS 24658 spores derived from a preculture in a tube of slanted nutrient agar.

After 3 days at 24° C. with shaking, 1 ml of a 4% strength ethanolic solution of nitroglycerine is added to the culture medium. After 10 days, a 50% yield of GMN-1 and GMN-2 mixture is obtained, with an equal proportion of GMN-1 and GMN-2.

EXAMPLE 7

Conversion of nitroglycerine to glyceryl 1-mononitrate and glyceryl 2-mononitrate by a culture of the protozoon Tetrahymena thermophila B4-1868

1—Culture setup

Composition of the culture medium

| bactopeptone | 20 g/l |
|---|---|
| D-glucose | 5 g/l |
| yeast extract | 1 g/l |
| MgSO$_4$.6H$_2$O | 0.25 g/l |
| KH$_2$PO$_4$ | 0.5 g/l |
| ferric EDTA | 30 mg/l |

Sterilization at 115° C. for 20 minutes.

Inoculation of 50 ml of medium in a 250 ml conical flask with 1 to 2 ml of an aqueous suspension of *Tetrahymena thermophila* B4-1868.

The resulting culture is thermostated at 28° C. and maintained with gentle and linear shaking (of the order of 100 cycles per minute).

The cells are counted under a microscope. 2—Bioconversion

Addition of 33 μmol of nitroglycerine in a 4% strength solution in ethanol when the culture has reached a density of $35 \times 10^5$ cells per 50 ml of medium.

Shaking and temperature are maintained under the same conditions as for the culture. The development of the bioconversion as a function of time is monitored by HPLC of aliquot parts of the supernatant.

3—Extraction

Following the same procedures as in the previous examples.

4—Results

The results are given in μmol under the conditions described in Example 1 and are collated in Table 6.

TABLE 6

Bioconversion of nitroglycerine by *Tetrahymena thermophila* B4-1868

| Time (days) | Number of cells | GMN-2 μmol | GMN-1 μmol | GDN-1,3 μmol | GDN-1,2 μmol | GTN μmol |
|---|---|---|---|---|---|---|
| 0 | 35.10⁵ | — | — | — | — | 33 |
| 1 | 30.10⁶ | 9.5 | 8.6 | 7 | 10 | <1 |
| 2 | 5.10⁷ | no result | 5.5 | 9 | 20 | <1 |
| 3 | 10⁷ | 5.7 | 5.3 | 7.7 | 14 | <1 |
| 6 | 10⁶ | 7 | 6.6 | 7.4 | 12 | <1 |

The hydrolysis of nitroglycerine by *Tetrahymena thermophila* B4-1868 is rapid and efficient; it leads to a more or less equimolar mixture of glyceryl mononitrates. However, the substrate and the products obtained are strongly diluted in order to preserve the survival of the protozoan. If a dose of 70 μmol of nitroglycerine (in 4% strength ethanolic solution) is applied per 50 ml, that is to say 1.4 millimolar, the cells die during the first day while completely hydrolysing the nitroglycerine.

EXAMPLE 8

Conversion of nitroglycerine to glyceryl 1-mononitrate and glyceryl 2-mononitrate by a culture of the yeast *Rhodotorula glutinis* ATCC 15125

1—Culture set-up

Composition of the medium identical with that of Example 1.

Sterilization of the medium at 115° C. for 20 minutes.

Inoculation of 50 ml of medium in a 250 ml conical flask with a small quantity of *Rhodotorula glutinis* ATCC 15125 cells.

The resulting culture is thermostated at 24° C. and maintained with continuous shaking (rotary shaker, 180 revolutions/minute).

2—Bioconversion

Addition of 1 ml of a 3% strength nitroglycerine solution in ethanol (107 μmol) 3 days after the inoculation.

The incubation takes place under the same conditions as the culture.

The development of the bioconversion in the course of time is followed using HPLC of aliquot parts which have been treated previously on silica.

3—Extraction

Following the procedures described above. 4—Results

The results are expressed in μmol under the same conditions as those described in Example 1, and are collated in Table 7.

TABLE 7

Bioconversion of nitroglycerine by *Rhodotorula glutinis* ATCC 15125

| Time (days) | GMN μmol | GDN-1,3 μmol | GDN-1,2 μmol | GTN μmol |
|---|---|---|---|---|
| 0 | — | — | — | 107 |
| 1 | <1 | 22 | 6 | 72 |
| 2 | <1 | 39 | 27 | 62 |
| 3 | <1 | 43 | 38 | 47 |
| 4 | 8 | 30 | 28 | 40 |

CONCLUSION:

The yeast is able to hydrolyse nitroglycerine to glyceryl mononitrates. However, in this particular case, the reactions are slow.

We claim:

1. A process for the preparation of a glyceryl mononitrate or a mixture of glycerol mononitrates in a single step comprising a bioconversion step of nitroglycerine to glyceryl mononitrate or a mixture thereof by a microorganism selected from the group consisting of yeasts, fungi and protozoa.

2. The process of claim 1 wherein said microorganism is fungi.

3. The process of claim 1 wherein said fungi are selected from the group consisting of Cunninghamella, Goetrichum, Sporotrichum, Phanerochaete, Beauveria and Mucor.

4. The process of claim 3 wherein said fungi are selected from the group consisting of *Cunninghamella elegans, Geotrichum candidum, Sporotrichum paranense, Geotrichum exile, Phanerochaete chrysosporium Beauveria tenella, Beauveria bassiana* and *Mucor plombeus*.

5. The process of claim 1 wherein said protoza belong to the genus Tetrahymena, and said yeasts belong to the genus Rhodotorula.

6. The process of claim 1 wherein said microorganism is applied in free form, in bound form or in encapsulated form.

7. The process of claim 6 wherein said microorganis is applied in encapsulated form in a natural or synthetic polymer.

8. The process of claim 1 wherein said bioconversion step is carried out in a culture medium of said microorganism containing nitroglycerine.

9. The process of claim 8 wherein said nitroglycerine is added to said culture medium all at once, in a ratio of 2 to 5 millimoles per liter of medium.

10. The process of claim 8 wherein said nitroglycerine is added to said culture medium all at once, in a ratio of 3 to 4 millimoles per liter of medium.

11. The process of claim 8 wherein said culture medium contains:

| yeast extract | 4 to 20 g/l, |
| malt extract | 5 to 15 g/l and |
| sterilized glucose | 2 to 20 g/l. |

12. The process of claim 8 wherein said bioconversion step is carried out at a temperature ranging from 20 to 50° C. and wherein the pH of said culture medium ranges from 3 to 8.

13. The process of claim 1 wherein predominantly glyceryl 2-mononitrate is prepared using *Sporotrichum paranense* or *Phanerochaete chrysosporium*.

14. The process of claim 1 wherein predominantly glyceryl 1-mononitrate is prepared using *Cunninghamella elegans, Beauveria tenella,* or *Geotrichum candidum*.

* * * * *